(12) United States Patent
Buschmann (10) Patent No.: US 6,298,253 B1
(45) Date of Patent: Oct. 2, 2001

(54) METHOD AND DEVICE FOR MEASURING THE ABSORPTION OF RADIATION IN A PORTION OF TISSUE

(76) Inventor: Johannes Paul Buschmann, Birkenleiten 9, 8000 Munchen 90 (DE)

( * ) Notice: Subject to any disclaimer, the term of this patent is extended or adjusted under 35 U.S.C. 154(b) by 0 days.

(21) Appl. No.: 07/573,225
(22) PCT Filed: Feb. 24, 1989
(86) PCT No.: PCT/EP89/00170
    § 371 Date: Sep. 21, 1990
    § 102(e) Date: Sep. 21, 1990
(87) PCT Pub. No.: WO89/09016
    PCT Pub. Date: Oct. 5, 1989

(30) Foreign Application Priority Data

Mar. 24, 1988 (DE) ................................................ 38 10 008

(51) Int. Cl.[7] ........................................................ A61B 5/00
(52) U.S. Cl. .................... 600/338; 600/339; 600/310; 600/322; 600/342
(58) Field of Search .................................... 128/633, 634, 128/664, 685, 666

(56) References Cited

U.S. PATENT DOCUMENTS

| | | | |
|---|---|---|---|
| 4,856,527 | * 8/1989 | Karcher et al. | 128/634 |
| 4,907,876 | * 3/1990 | Suzuki et al. | 128/633 |
| 4,913,151 | * 4/1990 | Harui et al. | 128/634 |
| 4,925,299 | * 5/1990 | Meisberger et al. | 128/633 |
| 4,938,218 | * 7/1990 | Goodman et al. | 128/633 |

FOREIGN PATENT DOCUMENTS

0135840 * 4/1985 (EP) ..................................... 128/633

* cited by examiner

*Primary Examiner*—Eric F. Winakur
(74) *Attorney, Agent, or Firm*—Pendorf & Cutliff (57) ABSTRACT

Device and method for measuring the absorption of radiation in a portion of tissue. For monitoring tissue and/or in order to permit medical indications, it is necessary to gather parameters allowing an assessement of the condition of the tissue, especially with regard to its oxygen supply. The disclosed invention provides a sensor carrier (1) at the loose end of which a sensor device (2) is mounted. This sensor device carries sensor areas (5, 6) which are connected to a measuring instrument (4). Light is emitted from a sensor area (5) and received by a sensor (6) after having transilluminated the tissue. The disclosed invention may be used for examining and controlling the tissue, for example, for perinatal measurement of arterial oxygen saturation of the fetus.

32 Claims, 5 Drawing Sheets

METHOD AND DEVICE FOR MEASURING THE ABSORPTION OF RADIATION IN A PORTION OF TISSUE

This invention relates to a method and device for measuring the absorption of radiation in a portion of tissue) using in particular a sensor device which comprises two sensor areas for transilluminating a portion of tissue wherein said sensor areas are connected to a measuring instrument and with one of them being conceived as radiation emitter and the other being conceived as radiation sensor.

When monitoring physiological or biochemical data about biological tissue, the aim of a continuous registration of data is to determine such data directly and as precisely as possible.

When preparing and/or surveying childbirth it is desirable to survey the physical condition of the fetus continuously and to have data at hand which allow an assessment of the present state of the child and in particular of fetal oxygen supply.

Up to now a current method of surveying the fetus is to monitor its heart rate continuously, either by a fetal electrocardiogram or by registering movements which are synchronous with the heartbeat by means of ultrasound. However, changes of the fetal heart rate—even when judged in correlation with uterine contractions—are not very reliable indicators of fetal well-being.

The prior art also offers the possibility of continuously measuring fetal partial pressure of $O_2$ and $CO_2$. Although these parameters are interesting from a clinical point of view, the employed measuring techniques involve considerable theoretical and practical disadvantages which do not allow their routine use:

Apart from the fact that such transcutaneous measurements often do not present the necessary precision and reproducibility, a further disadvantage is that the diameter of the probes is relatively large. This does not allow their introduction until the orifice of the uterus is already relatively wide open. A further disadvantage is the necessity of visual control when attaching the probes to the fetal skin and with it the fact that a "vaginal adjustment" is required for both their positioning and control. Another disadvantage with this measuring method is that the skin needs a rather considerable warming-up in order to obtain a hyperemia. During prolonged measuring periods this warming-up may involve skin damage.

A further possibility of the prior art is to measure oxygen saturation of the blood optically and transcutaneously by transilluminating a portion of tissue. With this method, appropriately chosen radiation wavelengths allow determination of the percentage of hemoglobin carrying $O_2$. This kind of measurement requires a measuring device which can be placed around part of the body for transilluminating the same. The prior art applies such measuring devices on a finger or an ear-lobe.

Patent Application No. EP-A2-135 840 describes a measuring device which allows measurement of the oxygen level of fetal blood by introducing a sensor carrier into the vagina. The loose end of the sensor carrier is provided with a sensor device suitable for placement on the fetus. Measurement is made by reflection from the fetal tissue, with the sensor device being placed on the surface of the fetal body, e.g. somewhere on the head. A disadvantage of this measuring device is the fact that there is no true optical transillumination of the tissue. There is only a reflection which is effected by a light emitter which emits light onto the surface of the fetal tissue. As the light receiver is mainly placed beside the light emitter, i.e. also outside the tissue in question, essentially there is no real transillumination of or transmission through the tissue.

Patent Application No. GB-A-2 155 618 describes a measuring device which is also simply placed on the surface of the fetal body, just as the measuring device described in Patent Application No. EP-A1-247 777.

The objective of this invention is to provide a method and a device of the kind already described at the beginning of this document and to allow a precise monitoring of data with biological tissue. The method and device distinguish themselves at the same time by their simple construction and reliable practicability.

As described in this invention, the objective is met by means of at least one sensor area which is or can be introduced into the tissue for transilluminating the same.

The device and the method of this invention offer a number of considerable advantages. In accordance with this invention at least one sensor area is invasively stuck into the tissue. This guarantees that the tissue is adequately transilluminated and that the obtained absorption of radiation is such as to furnish the required parameters. The tissue is hardly impaired by the measurement, and blood-perfusion, for example, is not disturbed.

The disclosed invention thus offers a particularly precise way of determining or monitoring oxygen saturation or oxygen supply of the tissue. For example, the disclosed invention is suitable, as will be described hereinafter, for monitoring a child during birth. The disclosed invention can, however, also be applied for monitoring the oxygen supply of experimental tumors in the field of cancer research, the oxygen supply of the heart in the field of infarct research, or the oxygen supply of persons exposed to extraordinary ambient conditions, as is, e.g., the case with high-performance athletes or people working in rooms with a reduced oxygen level and an associated risk of suffocation. In the latter application, a signalling or warning device can be connected to the device of the disclosed invention.

Furthermore, the method and device of this invention make it possible to monitor the blood-perfusion of organs and skin lobes in a particularly simple way, for example intra- or post-operatively, for example after transplantations, plastic surgery, vessel- and bypass operations. As already mentioned, another possibility is the application for perinatal monitoring.

With this invention, at least one sensor area is stuck invasively. Possible embodiments of this invention allow an invasive sticking of either the radiation-emitting or the radiation-receiving sensor area alone or of both sensor areas.

The disclosed invention preferably uses the pulsatile share of absorption as a parameter since with this pulsatile share a particularly simple determination of influences originating from blood-perfusion is possible.

In a particularly advantageous embodiment of this invention the radiation for transilluminating the tissue is selected within a wavelength range between 0.1 and 20 $\mu$m.

This advantageous embodiment of this invention provides that radiation wavelengths (at least 2) for determination of hemoglobin fractions are selected so as to allow, for example, deducting values for sHb, $sHbO_2$, sHbCO), $sHbCO_2$, sHbS, sMet-Hb, sHbF, etc.

For attaching the sensor device on the tissue, it may be convenient to mount the same on an oblong sensor carrier which can, for example, be introduced into the vagina.

In order to guarantee the safe emission and sensing of the radiation and to avoid any electrical interference, the use of an optical fiber may be particularly suitable for emitting and/or sensing radiation. In such a case, the radiation source can either be placed on the sensor device or in a remote pertinent measuring instrument.

This invention also includes the possibility of placing the radiation source(s) directly on the surface of the tissue so that no optical fiber is required for at least one sensor area. The transmitted radiation can be registered by means of an electro-optical converter directly on the surface of the tissue or in the measuring device if an optical fiber is used.

Another possibility is to stick electro-optical converters into the tissue invasively. In a particularly advantageous configuration of this invention both the radiation emitter and the radiation sensor can be arranged on a single-piece sensor carrier, for example on a needle. It is, however, also possible to place the radiation emitter or the radiation sensor on a separate puncture-element carrier. The type and choice of the respective light sources or light sensors can be adapted to the respective requirements without any problem; it is, for example, possible to use incandescent lamps, light-emitting diodes or laser diodes etc. for illumination.

Since the sensor carrier in this invention is introduced directly into the vagina, the sensor device can be placed onto the fetal head at a very early stage of childbirth. This allows a monitoring of the fetal oxygen supply over a long period which, in turn, allows an early decision on or initiation of possible therapeutical steps, e.g., a Caesarian section or other delivery modalities.

A further essential advantage of the disclosed invention is that the optical transillumination of a portion of fetal tissue furnishes significant data with regard to fetal oxygen supply. Since the oxygen supply represents a parameter which reacts more quickly than other parameters and reflects multiple factors, e.g., problems with the placenta or the umbilical cord, uterine contractions and fetal distress, the monitoring of fetal oxygen supply allows a direct assessment of the overall fetal state at any time. Moreover, the amplitude of the pulsatile signal or its integral value taken over the monitoring time allows an assessment of blood-perfusion and correlates in a clinically reliable manner with a centralization of fetal circulation, i.e. with a possible fetal shock.

A further advantage of this invention is that the transillumination of a portion of fetal tissue is based on a physical principle which distinguishes itself through its reduced susceptibility to problems and through its quick action. This allows an immediate detection of an error in case of inadequate positioning of the sensor device.

A further essential advantage of this invention is the fact that the disclosed device can remain on the child over a prolonged period without causing any inconvenience or damage to the fetal tissue during measurement. Consequently, there is no need to shift or re-attach the device after a certain time. On the one hand, this avoids complicated and time-consuming mounting procedures. On the other hand, it allows a continuous monitoring of the entire birth process once the whole device has been set and adjusted.

A particularly beneficial advantage of the invention is that the radiation-emitting sensor area emits at least two different wavelengths which are received by the sensor. The disclosed invention thus makes it possible to carry out one measurement with a wavelength suitable for determining the total hemoglobin level of the blood (isobestic point), whereas the second measurement is made at a wavelength appropriate for determining the oxihemoglobin. As the transmission in the infrared range depends on the hemoglobin level of the transilluminated tissue and since other factors, such as thickness of the skin, influence the transmission, this method allows the determination of just the transmission value which reflects blood-perfusion and the elimination of the absolute transmission or penetration values of the transilluminated tissue.

In this invention, the measuring instrument is balanced at the beginning of the measuring process in order to eliminate constant, non-pulsatile signals, for example by means of an AC-signal coupling. This allows a precise determination of oxygen saturation of the blood.

At least one light source and at least one light-sensitive element are appropriately placed near the sensor device. In such a configuration of the mesuring device, the sensor device can be connected to the measuring instrument by electrical lines and thus allows conversion of electrical energy into optical signals or reconversion of optical signals into electrical signals in the immediate vicinity of the sensor device. The use of miniaturized photo-electric semiconductors allows a considerable miniaturization of the sensor device as a whole.

Another possible configuration of this invention which is particularly convenient for various applications is a connection of the sensor areas with a light source or a light-sensitive element placed at the end of the sensor carrier by means of optical fibres. The use of small-diameter optical fibres allows not only a reduction of the size of the sensor device and the sensor carrier but also the possibility of using larger and/or more efficient photo-sensors or light-emitting elements.

A further advantage when using optical fibres is that electromagnetic interference has no influence on data transmission from the sensor areas. Measurement reliability is thus considerably increased. Furthermore, at least the sensor carrier and the sensor device with its sensor areas are disposable articles. In order to keep costs in hospitals low, the cost of disposable articles must also be kept as low as possible. Due to their low cost, optical fibres are particularly suitable also from this point of view. A further advantage of optical fibres is that they are very flexible and thus do not impair the movement of the sensor device or the sensor carrier.

It is moreover possible to choose a very low diameter for the optical fibres which, in turn, results in a high degree of miniaturization. A further and very important advantage of the use of optical fibres stems from their safety as they cannot conduct any dangerous electric currents.

In order to allow a safe fastening of the sensor device on the tissue or on the fetal body, it is particularly appropriate to provide the sensor area with a double spiral which can be screwed into the fetal tissue and the end of which carries the sensor areas. In order to facilitate the screwing in of the double spiral it may be convenient to design the sensor carrier as a flexible shaft.

A further, also very convenient feature of the disclosed device is a sensor device provided with a spiral which carries a sensor area and which allows attachment to the fetal tissue in a fashion similar to that of a fetal ECG scalp electrode. This spiral allows safe screw-like attachment and anchoring. Also, it may be advantageous to use a flexible shaft as sensor carrier. An invasive pin may be used as second sensor area.

For the spiral or the pin an appropriate embodiment is a columnar tubing, similar to a syringe cannula, which encloses one or several optical fibers. It is thus possible to use a spiral or a pin of sufficient strength and to make sure at the same time that radiation emission or sensing is possible at the end of the spiral or pin.

In a further beneficial configuration of the sensor device, the sensor areas are placed on the sensor device and the sensor device includes an additional anchoring device which allows grasping the tissue. For the anchoring device, a screw-in spiral or a needle suitable for puncturing the tissue can be used. One of the advantages of this configuration is that the anchoring device itself has no measuring task and therefore can be perfectly adapted to each particular application.

A further advantage of this invention with regard to sensor device attachment is obtained by placing the sensor areas on a clamp which allows grasping the tissue. This version avoids lesions of the skin or tissue when introducing a sensor area. The described clamp allows, for example, grasping limbs, such as part of a foot or a finger. An alternative of this version is a clamp with pointed front edges. This allows puncturing the fetal tissue and achieving a transillumination of an undisturbed blood-perfused portion of tissue, in a similar manner as with the sensor devices described above.

In accordance with this invention, it may also be convenient to fasten the sensor device, and with it the sensor areas, on the body of the tissue by means of glue or by using the suction force of vacuum.

A further advantageous embodiment of this invention is a flexible sensor carrier placed in a preshaped guide tube. The guide tube may be bent or preshaped in such a manner as to facilitate introduction of the device into the vagina, thereby also increasing accuracy of positioning.

In a further, very convenient version the sensor device and the sensor carrier can be uncoupled mechanically, without affecting data transmission. This is advantageous if the sensor device has been screwed or inserted into the tissue by means of an anchoring device. The mechanical uncoupling eliminates the risk of an unintentional loosening of the anchoring. The mechanical uncoupling is made possible by disengaging form-fitting, engaged segments, for example, by retracting the sensor carrier.

In a further advantageous configuration of the applicance for use on a child, an additional device for tocometry can be connected to the measuring instrument. For this, common tocographical equipment may be used. An ideal apparatus, easily possible with this invention, would be one provided with a monitor showing not only the intensity of uterine contractions but also the respective oxygen level of the fetal blood. Instead of or in addition to the intensity of uterine contractions it is also possible to show the fetal EKG.

Hereinafter the disclosed invention is described by means of various configuration examples together with the respective drawings, in which.

Figure 1:
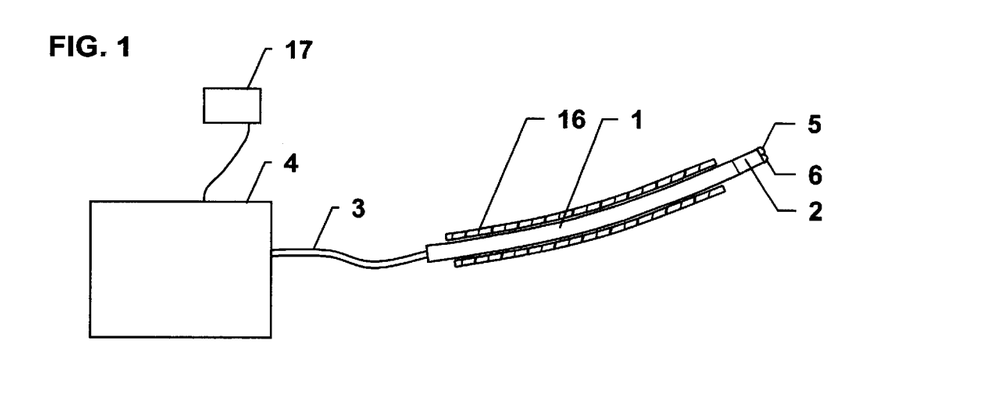
FIG. 1 is a schematic illustration of the measurement device of this invention.

FIG. 1 is a schematic illustration and shows one possible version of the appliance of the disclosed invention. The measuring device comprises a measuring instrument 4 which, in order to simplify illustration, has only been shown as a black box. A sensor device mounted on an oblong sensor carrier 1 is connected to the measuring instrument 4 by means of connecting lines 3. The length of the sensor carrier 1 is such as to allow its transvaginal introduction and to allow the establishment of a contact between sensor device and fetal body. At the loose end of sensor device 2, sensor areas 5 and 6 are placed. The latter will be described in detail hereinafter.

The disclosed invention also includes the possiblity of connecting a sensor device 17 to the measuring instrument 4 for determination of the intensity of uterine contractions (tocography), in order to allow an assessment of both the oxygen level of fetal blood and uterine contractions of the mother. As an alternative or in addition to monitoring uterine contractions, it is also possible to make an electrocardiogram of the child. In this case, the electrode to be fastened on the child can be integrated in one of the sensor areas 5 or 6. As usual, the other electrodes necessary for the EKG can be fastened on the body of the mother.

Normally the diameter of the sensor carrier 1 will be as small as possible in order to allow its introduction with only a small opening of the uterus orifice. Sensor device 2 preferably has the same outside diameter as sensor carrier 1.

For some of the examples of possible sensor devices of this invention described hereinafter it may be convenient to choose a flexible shaft for sensor carrier 1 as this allows turning sensor device 2. In order to obtain sufficient rigidity on one hand, and to facilitate attachment of sensor device 2 on the other, sensor carrier 1 may be housed in a preshaped guide tube 16 which has been adapted to the prevailing anatomic circumstances.

Figure 2:
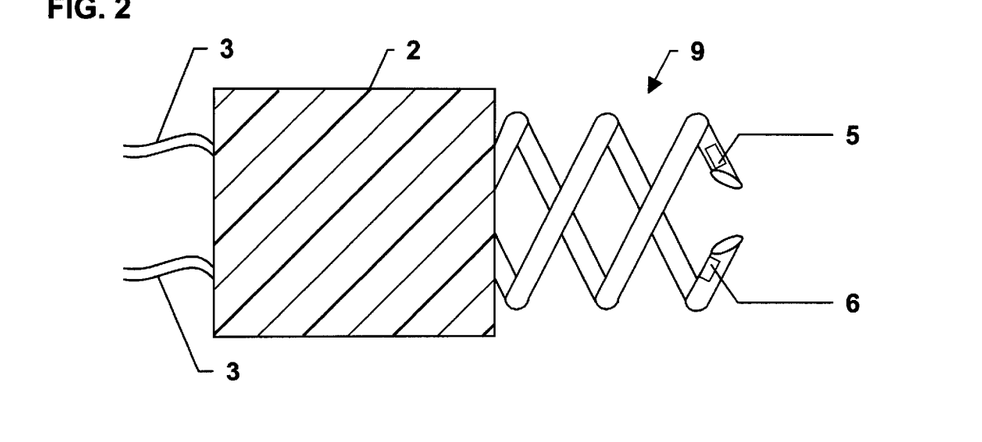
FIG. 2 is a schematic illustration of possible versions of the sensor device.

FIG. 2 shows one possible version of sensor device 2 of the disclosed invention. At its loose end, sensor device 2 carries a double spiral 9 at each end of which sensor areas 5, 6 are placed. With this configuration, sensor area 5 emits radiation which can be received by sensor area 6. In this case it is convenient if emitter 5 emits two different light wavelengths, for example one wavelength adapted to the total hemoglobin level and one wavelength adapted to the oxyhemoglobin. Sensor device 2 is put on the fetal skin and turned, thereby screwing the double spiral 9 into the fetal tissue. In this way, a portion of tissue is enclosed between emitter 5 and sensor 6. Part of the light emitted from emitter 5 thus reaches sensor 6, and part of the light is absorbed by the fetal tissue. As already described above, the absorption rate allows a determination with regard to the hemoglobin level.

Figure 3:
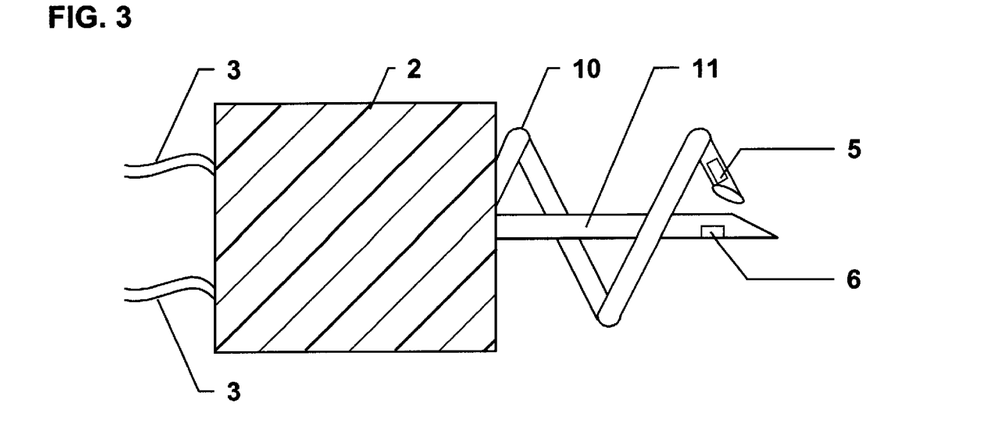
FIG. 3 is a schematic illustration of possible versions of the sensor device with only one sprial.
Figure 4A:
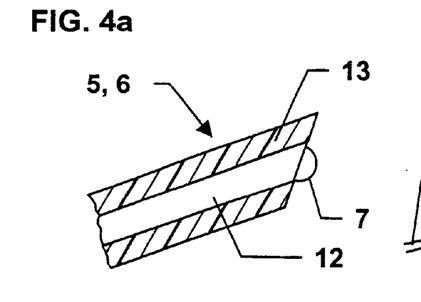
FIG. 4a is a partial view of a possible version of a sensor area.
Figure 4B:
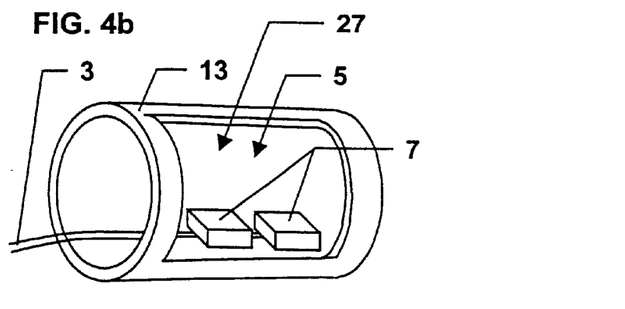
FIG. 4b is a partial view of another possible version of a sensor area.
Figure 4C:
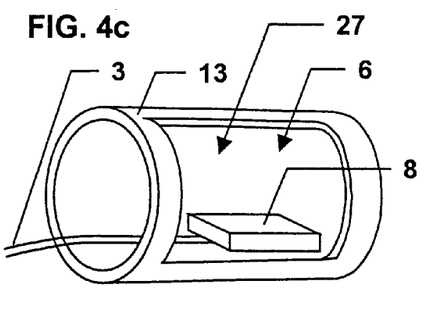
FIG. 4c is a partial view of another possible version of a sensor area.
Figure 4D:
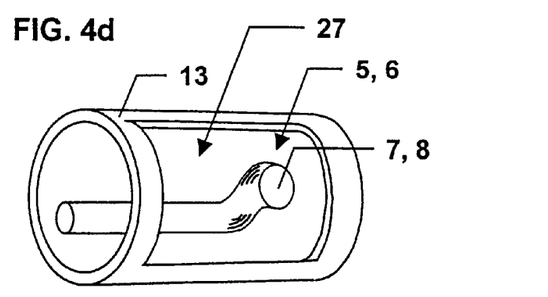
FIG. 4d is a partial view of another possible version of a sensor area.

FIG. 3 shows a further embodiment of the sensor device of this invention with only one spiral 10. A pin 11 is arranged concentrically with this spiral. The sensor areas 5 and 6 are provided at the loose ends of pin 11 of spiral 10. In the configuration shown, emitter 5 is arranged at the end of spiral 10 whereas sensor 6 is mounted at the end of pin 11. The execution may, however, also be vice versa. In this configuration of the sensor device, pin 11 penetrates the fetal tissue when sensor device 2 is turned and spiral 10 is screwed into the fetal tissue.

FIG. 4 is a large-scale sectional view of the end area of one of the spirals shown in FIGS. 2 and 3, or of pin 11. As shown in FIG. 4, these consist of a hollow body 13, e.g. a tube, housing an optical fibre 12. Consequently, at the end of the hollow body 13 there is a schematically illustrated light source 7 or the end of an optical fiber for the emission of light. A similar configuration is possible for sensor 6, with a light-sensitive element 8 or the end of an optical fiber (see FIG. 8) being provided instead of light source 7.

Figure 5A:
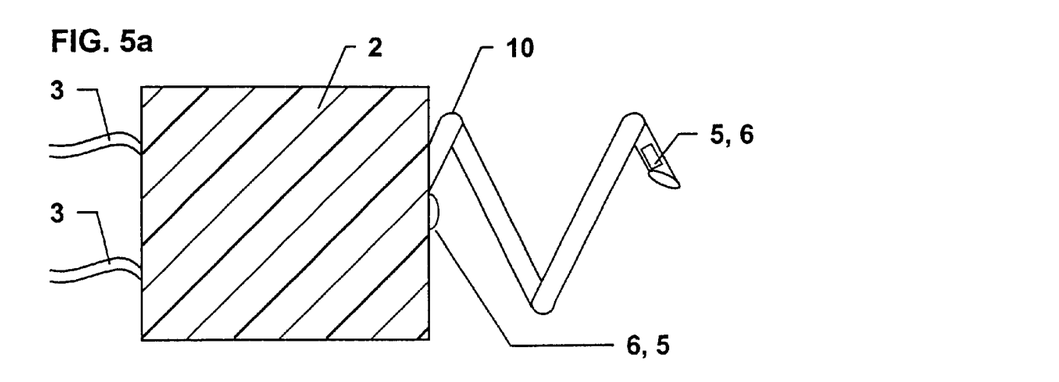
FIG. 5a is a further possible version of a sensor device of this invention.

Unlike the configuration shown in FIG. 3, configuration shown in FIG. 5a has only one sensor area, viz. sensor area 5, which can be invasively stuck into the tissue whereas the other sensor area 6 is held in place against the surface of the tissue when sensor area 5 is invasively screwed in. This may, however, also be executed vice versa. This execution guarantees, on the one hand, an exact anchoring of sensor device 2 and allows, on the other hand, limiting invasive sticking to one sensor area.

Figure 5B:
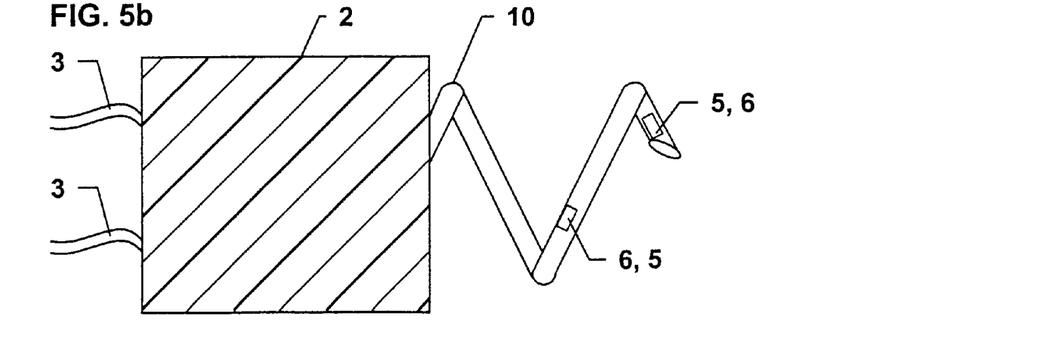
FIG. 5b is a further possible version of a sensor device of this invention.

FIG. 5b shows both sensor areas located in the same sensor carrier, for example an needle.

Figure 6:
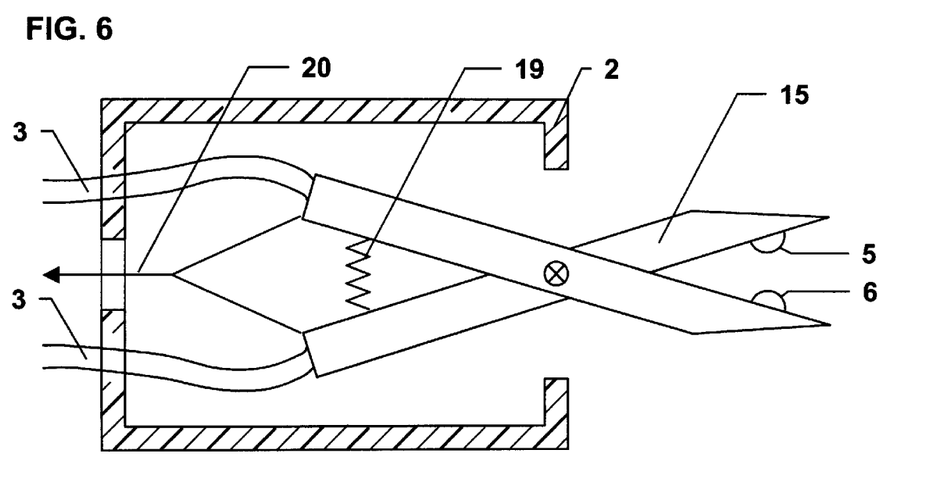
FIG. 6 is an example of a possible version of a sensor device comprising a clamp.

An alternative embodiment of sensor device 2 is illustrated in FIG. 6 and comprises a clamp 15 at its loose end which carries sensor areas 5 and 6 respectively. By means of a spring element 19 it is possible to pretighten the open or closed clamp 15. A pulling device allows decreasing the distance between sensor areas 5 and 6. This configuration permits seizing part of the fetal body with clamp 15 and positioning it between sensor areas 5 and 6. The pulling device 20 can be provided with a lock (not shown) in order to avoid an undesirable opening of the clamp 15. In order not to disturb blood-perfusion when seizing a portion of fetal tissue with the clamp, the latter may be pointed at its front end to allow a puncturing of the fetal tissue, as with the double spiral shown in FIG. 2.

Figure 7:
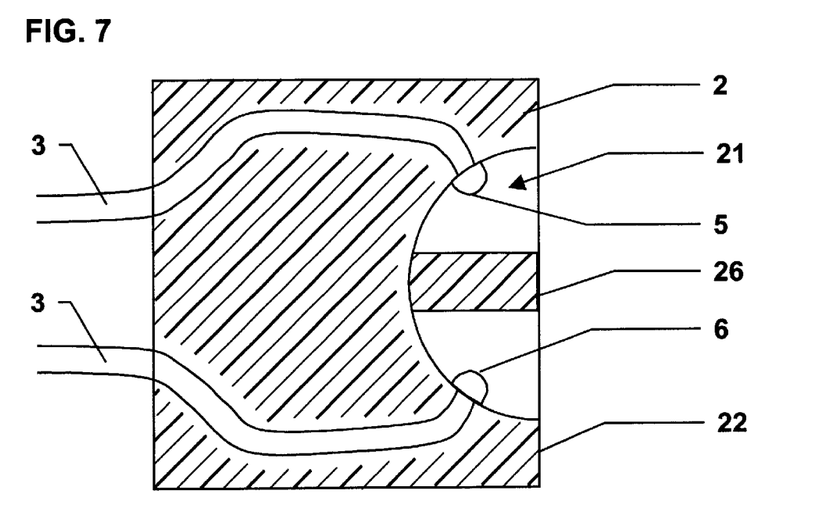
FIG. 7 is an example of a possible version of a sensor device to be fastened to the fetal body using adhesive.

A further embodiment of the disclosed sensor device is illustrated in FIG. 7. In this configuration the sensor device has a cavity 21 at its front end, as in the configuration shown in FIGS. 8, 9 and 10. This cavity may also be a concave spherical segment. Sensor areas 5 and 6 are placed in this cavity in such a manner as to allow transillumination of the fetal tissue pressed into cavity 21. In this configuration the sensor device has a larger front surface 22 for gluing onto the fetal body.

Figure 8:
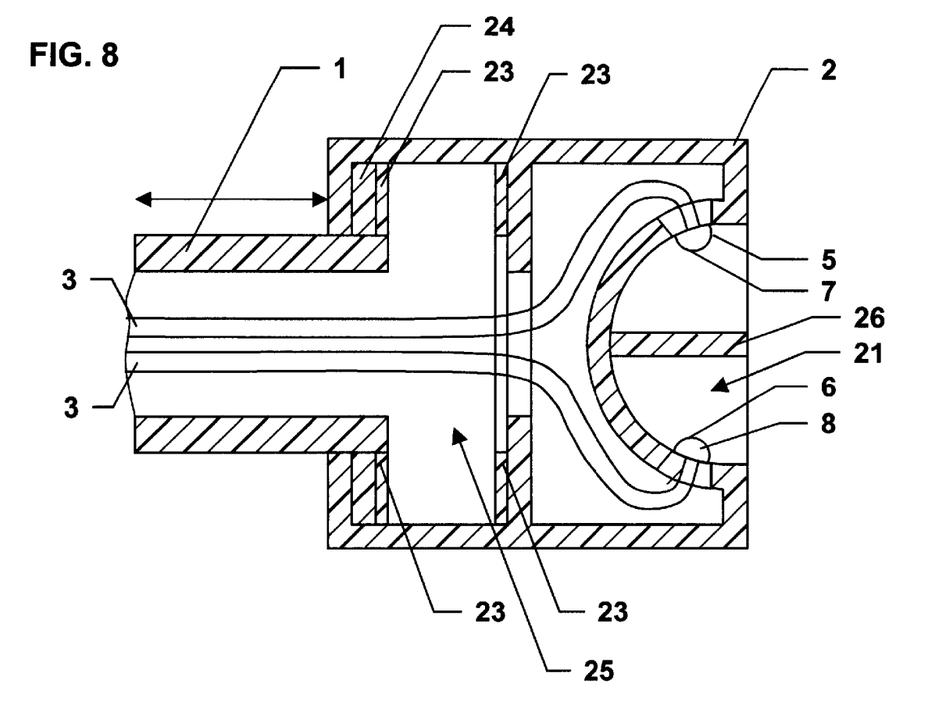
FIG. 8 is a schematic sectional view of the connection between a possible embodiment of the sensor device of this invention and the sensor carrier.

FIG. 8 is a schematic illustration of a further alternative embodiment of sensor device 2 and of part of the end of sensor carrier 1. As provided in the configurations described above, sensor carrier 1 consists of a tube and houses the connecting lines 3 which connect sensor areas 5 and 6 to the measuring equipment. The connecting lines 3 may consist of optical fibres. In this case the light source and the light sensor can be arranged either on the measuring equipment 4 or at the end of sensor carrier 1.

Another possibility is to use electrical cables as connecting lines 3 and to convert electrical energy into radiation and to reconvert radiation by means of a sensor directly at the sensor areas 5 and 6. At its loose end, sensor carrier 1 is provided with a flange 24 This flange has form-fitting elements, e.g. toothing, and is placed in cavity 25 of sensor device 2 in such a manner as to allow an axial shifting of flange 24, and thereby of sensor carrier 1, in relation to sensor carrier 2. In the arrangement shown in FIG. 8, flange 24 is in a retracted position. Consequently its form-fitting elements 23 are not in contact with the form-fitting elements 23 at the front side of cavity 25 of sensor device 2. If, in this configuration, sensor carrier I remains in its previous position. If a turning of sensor device 2 is desired, sensor carrier 1 and thus its flange 24 must be moved forward (to the right in the figure) in order to connect the form-fitting elements 23.

In order to prevent unwanted radiation transfer between the two sensor areas 5 and 6 of the possible embodiments shown in FIGS. 7, 8, 9 and 10 without prior transillumination of the fetal tissue, i.e., to keep light from reaching sensor 6 directly from emitter 5, an additional shielding 26 can be provided In cavity 21. In this case, the light originating from emitter 5 is directed on blood-perfused portions of the fetal body, and is reflected and transmitted back to sensor 6. This embodiment of the sensor device may be preferred in order to avoid a compression of the blood-perfused tissue and an ensuing disturbance of blood-perfusion.

Figure 9:
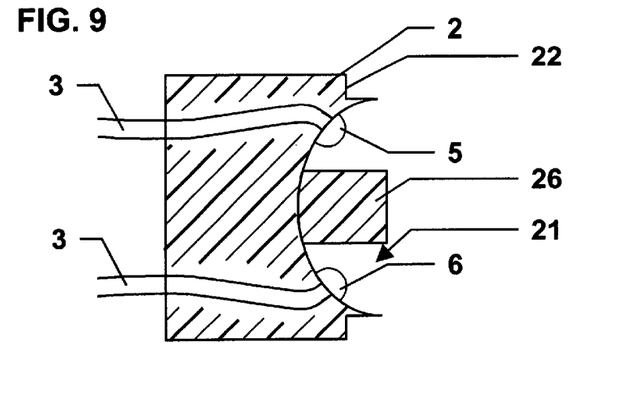
FIG. 9 is a sectional view of a further possible configuration, essentially corresponding to the configuration shown in FIGS. 7 and 8.
Figure 10:
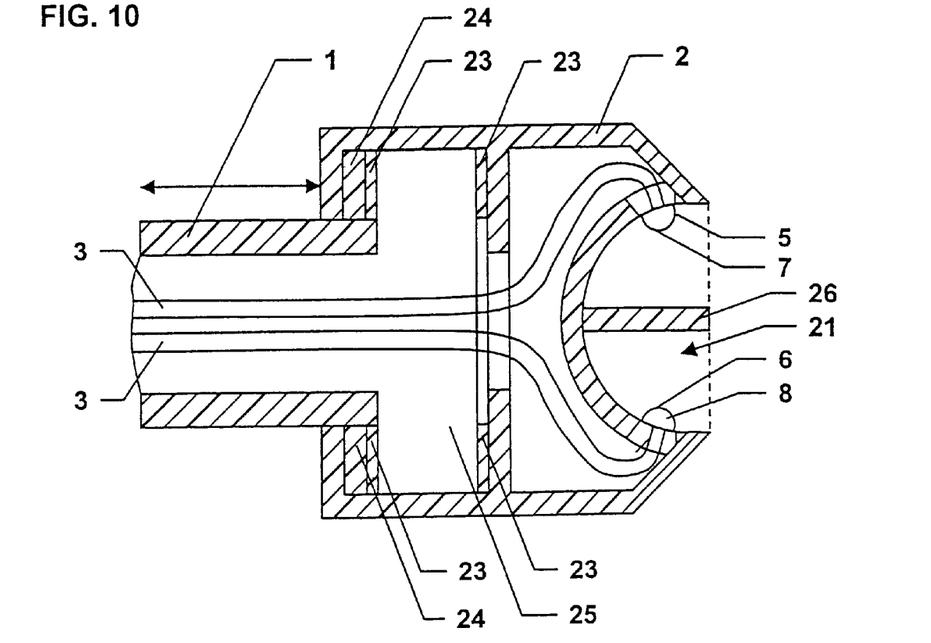
FIG. 10 is a sectional view of a further possible configuration, essentially corresponding to the configuration shown in FIGS. 7 and 8.

The possible embodiments shown In FIGS. 9 and 10 essentially correspond to the configurations shown in FIGS. 7 and 8, however, they differ from the latter in the pointed front end of sensor device 2 which allows an invasive sticking into the tissue to be transilluminated.

Figure 11:
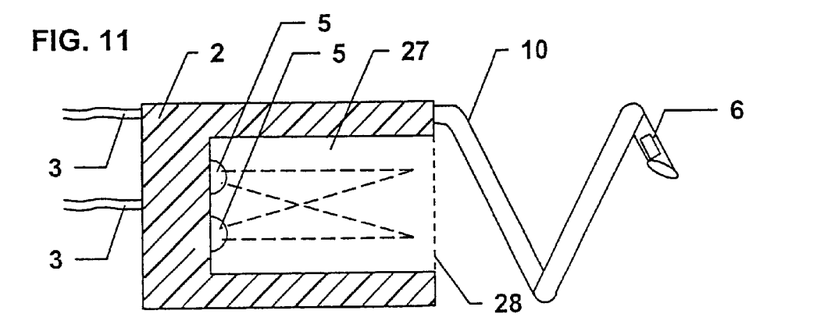
FIG. 11 is a sectional view of a further possible configuration of the sensor device of this invention.

FIG. 11 shows a sectional view of a further possible version which, with regard to its basic setup, is similar to the configuration in FIG. 5. At its front end, sensor device 2 carries a spiral 10, at the end of which there is a sensor 6. Inside the sensor device 2 there is a radiation-transparent body 27 which has a radiation-transmissive area 28. This area can, for example, be applied on the fetal skin and be anchored on the fetal tissue by means of spiral 10. Instead of body 27, it is also possible to provide a hollow body. At the bottom end of body 27 there are two sensor areas 5 which are both radiation emitters. They communicate by connections 3 which may be optical fibres or electrical lines. The two radiation emitters 5 emit radiation, each of them at a different wavelength. This radiation spreads conically in body 27 (see dotted line in FIG. 11). As a result, the two wavelengths mix in the area of the emergence or contact surface 28. This assures that radiation emission and respective radiation entry into the tissue takes place over a relatively large area. Should the radiation be partially screened off or impeded on its way by obstacles in the tissue, such as blood vessels, this does not negatively influence transillumination and still guarantees a sufficient sensor with a particularly large surface.

Figure 12:
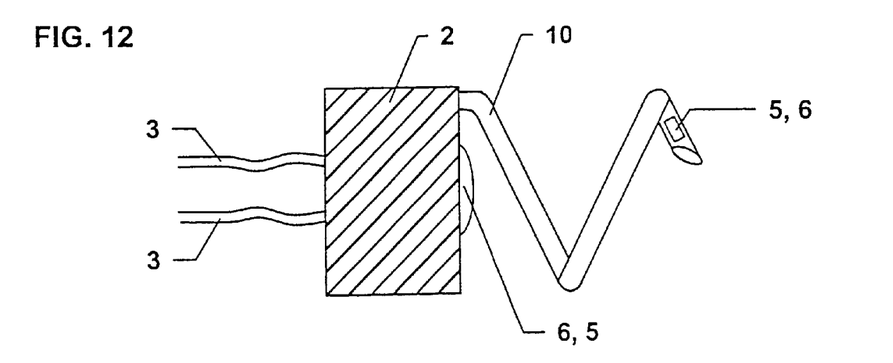
FIG. 12 is a sectional view of a further possible configuration.

FIG. 12 shows a sectional view of a further possible configuration which, in its basic setup, is also similar to the version in FIG. 5. At its front end, sensor device 2 is provided with a spiral 10 which, in its turn, carries an emitter 5 either on its windings or at its end. At the front end of sensor device 2 there is a radiation sensor 6. The particular advantage of this possible configuration consists in the possibility of providing the radiation sensor with a particularly large surface.

The disclosed invention is not limited to the embodiments shown in the above examples. On the contrary, this invention allows further configuration alternatives for the sensor device. This invention simply requires a radiation-emitting element to transilluminate a portion of tissue with the radiation being dected or received by a sensor or radiation-sensitive element in order to determine the rate of absorption.

The disclosed intention thus allows examining biological tissue of any kind. It can be used not only for monitoring childbirth but also in the field of research or for continuous monitoring. For supervision of childbirth, for example, the disclosed invention permits correlating the data from oxygen saturation determined in the above way with uterine contractions determined by means of tocographical equipment and/or fetal heart rate determined by means of a fetal EKG or ultrasound technique. This combination helps to eliminate error signals.

What is claimed is:

1. A method for measuring the intensity of light transmitted through a portion of living tissue carrying arterial blood comprising the steps of:
   providing at least two spaced sensor areas, at least one of which is a radiation emitter and at least one of which is a radiation receiver, and
   invasively introducing at least one sensor area into said living tissue in a manner whereby a portion of said living tissue is between the sensor areas for its transillumination,
   wherein the radiation emitter emits at least a first and a second wavelength which are received by the radiation receiver; and further including a step of selecting the wavelengths of the radiation in order to determine a hemoglobin fraction.

2. A method as in claim 1, wherein said emitter is selected from the group consisting of incandescent lamps, light-emitting diodes, and laser diodes.

3. A device for use in measuring radiation transmitted through a portion of living tissue comprising:
   at least two spaced sensor areas, with one of the sensor areas being constructed as a radiation emitter and the other sensor area being constructed as a radiation receiver for receiving radiation from the radiation emitter after transillumination of living tissue located between the sensor areas, and
   an evaluation unit, the sensor areas coupled to said evaluation unit,
   wherein at least one of the sensor areas further comprises a tissue penetrating carrier, and wherein the tissue penetrating carrier is in the form of a spiral for screwing into the tissue.

4. A device according to claim 3, wherein said tissue penetrating carrier comprises an optical fiber and a hollow cannula housing said optical fiber.

5. A device according to claim 3, wherein said hollow spiral needle contains at least two sensor areas.

6. A device according to claim 3, wherein said emitter sensor area includes a window in a steel needle.

7. A device according to claim 3, wherein said emitter sensor area is a light guide extending beyond a window in a steel needle.

8. A device for use in measuring radiation transmitted through a portion of living tissue comprising:
   at least two spaced sensor areas, one of the sensor areas being constructed as a radiation emitter for transilluminating living tissue located between the sensors areas, and the other senior area being constructed as a radiation sensor for sensing radiation from the radiation emitter;
   a measuring instrument, the sensor areas coupled to said measuring instrument, wherein at least one of the sensors areas further cover a tissue penetrating carrier; and means coupled to the radiation sensor for collecting information from the radiation sensor and for providing additional parameters including, at least, ECG.

9. A method of in vivo measuring radiation transmitted through a portion of living tissue comprising the steps of:
   providing a sensor device having at least two spaced sensor area, at least one of said two sensor areas comprising at least one optical fiber, said optical fiber being housed within a sensor carrier formed as a hollow spiral and terminating with a point, at least one of the sensor areas constituting the radiation emitter and at least one of the other of the sensor areas constituting the radiation receiver;
   screwing maid spiral sensor carrier with said optical fiber into said tissue whereby said carrier point and an end of said optical fiber enters said tissue to be transilluminated;
   analyzing radiation within the spectral range of between 0.1 $\mu$m and 20 $\mu$m, originating from said radiation emitter, and transmitted through the tissue, to transilluminate said tissue between said two sensor areas; and
   sensing maid transmitted radiation reaching said receiver.

10. A perinatal sensing system for determining the oxygen saturation of blood by the transillumination of living tissue, wherein light transmission in selected spectral ranges changes in intensity in response to different levels of oxygen saturation, comprising:
    means for generating light at an interstitial subcutaneous location within said tissue such that said generated light is transmitted to an epidermal location; and
    means for detecting changes in intensity of said light transmitted through to said epidermal location to determine an oxygen maturation within said tissue.

11. A perinatal sensing system for determining blood oxygen saturation by transillumination of living tissue, wherein the intensity of light transmitted in select spectral regions changes in response to different levels of blood oxygenation, comprising;
    means for generating light upon an epidermal location such that said generated light is transmitted to an interstitial subcutaneous location; and
    means at said interstitial subcutaneous location for detecting changes in intensity of said transmitted light in order to determine an oxygen saturation within said tissue.

12. A perinatal sensing system for determining blood oxygen saturation within body living tissue by transillumination wherein the light transmission changes in intensity in response to different levels of oxygen saturation, comprising:
    means for generating light at a first interstitial subcutaneous location within said tissue; and
    means for receiving light at a second interstitial subcutaneous location within said tissue in order to detect the changes in intensity of said light transmitted through said living tissue between said first and said second interstitial location in order to determine a the oxygen saturation of the blood.

13. A method for measuring the intensity of light transmitted through a portion of living tissue carrying arterial blood comprising the steps of:
    providing at least two spaced sensor areas, at least one of which is a radiation emitter and at least one of which is a radiation receiver, on a single-piece sensor carrier,
    invasively introducing at least one sensor area into said living tissue in a manner whereby a portion of said living tissue is between the sensor areas for its transillumination,
    emitting radiation from said radiation emitter, and
    measuring the amount of radiation absorbed between said emitter and receiver.

14. A method according to claim 13, wherein said single-piece sensor carrier is a hollow spiral needle.

15. A method for measuring the intensity of light transmitted through a portion of living tissue carrying arterial blood comprising the steps of providing at least two spaced sensor areas, at least one of which is a radiation emitter and at least one of which is a radiation receiver, and invasively introducing at least one sensor area into said living tissue in a manner whereby a portion of said living tissue is between the sensor areas for its transillumination, wherein the radiation emitter emits at least a first and a second spectral range which are received by the radiation receiver, wherein oxygen saturation is a function of both the pulsatile and the steady light absorption in said first and second spectral ranges, and wherein said first spectral range is adapted to measuring the total hemoglobin level and said second spectral range is adapted to measuring oxyhemoglobin.

16. A method for measuring the intensity of light transmitted through a portion of living tissue carrying arterial blood comprising the steps of:

providing at least two spaced sensor areas, at least one of which is a radiation emitter and at least one of which in a radiation receiver, invasively introducing at least one sensor area into said living tissue in a manner whereby a portion of said living tissue is between the Bangor areas for its transillumination, wherein said radiation receiver generates an electric signal which is, for each of said spectral ranges, proportional to the total transilluminated light within a spectral range, which signals comprises a constant, non-pulsatile signal component and a pulsatile signal component, performing calculations on the basis of said constant and said pulsatile Signals relative to said constant, non-pulsatile signal components of each spectral range from the total transilluminated signal, and generating from said calculations a value which is a function of the open saturation of the arterial blood.

17. A device for use in measuring radiation transmitted through a portion of living tissue comprising at least two spaced sensor areas, with one of the sensor areas being constructed as a radiation emitter and the other sensor area being constructed as a radiation receiver for sensing radiation transilluminated through living tissue from the radiation emitter, and a measuring instrument, the sensor areas coupled to said measuring instrument, wherein at least one of the sensor areas further comprises a tissue penetrating carrier, wherein one of said sensor areas is positionable in living tissue and is an electro-optical converter.

18. A device according to claim 17, wherein said electro-optical converter is an emitter selected from the group consisting of incandescent lamps, light-emitting diodes, and laser diodes or a receiver which is a miniaturized photosensitive semiconductor.

19. A perinatal sensing system for determining blood oxygenation within a body comprising:

means for generating light at an interstitial subcutaneous location within a body;

means for transmitting said generated light from said subcutaneous location to an epidermal location of a body, and means for detecting changes in intensity of said light transmitted through the tissue to said epidermal location wherein the transmitted light passing through the body changes in intensity in response to different levels of blood oxygenation; in order to determine blood oxygenation within said body.

20. A method for measuring the intensity of light transmitted through a portion of living tissue carrying arterial blood comprising the steps of:

selecting spectral ranges of radiation to be used to determine hemoglobin fractions in interest, providing at least two spaced sensor areas, at least one of which is a radiation emitter and at least one of which is a radiation receiver, wherein said radiation emitter sensor area emits at least a first and a second spectral range that are received by said radiation receiver, disposing at least one sensor area within said living tissue such that a portion of said living tissue is between said sensor areas for its transillumination, wherein said radiation receiver generates signals proportional to the light intensities received after transillumination of said living tissue in said respective spectral ranges, the signals comprising for each spectral range a constant, non-pulsatile signal component and a pulsatile signal component, and performing calculations on the basis of said constant and said pulsatile signal components of each of said spectral ranges to determine a value which is a function of the oxygen saturation of the arterial blood.

21. A method as in claim 20, wherein said hemoglobin fractions are selected from total hemoglobin, oxygenated hemoglobin, deoxygenated hemoglobin, methemoglobin, carboxyhemoglobin, and sulfhemoglobin.

22. A device for use in measuring radiation transmitted through a portion of living tissue, said device comprising a sensor carrier carrying two sensor areas, one of which is a radiation emitter and the other of which is a radiation receiver, said sensor carrier adapted for introducing at least one of said sensor areas into an interstitial subcutaneous location within a body, said radiation emitter transmitting light at a spectral range which changes in intensity in response to different levels of blood oxygenation saturation when passing in arteries and arterioles through said living tissue, said radiation receiver sensing said changes in intensity of said transmitted light.

23. A device as in claim 22, wherein said radiation emitter and radiation receiver are both provided in a single hollow needle.

24. A device as in claim 23, wherein said single needle is a hollow spiral needle.

25. A device as in claim 24, wherein at least one of said radiation emitter and radiation receiver are provided on the windings of said hollow spiral.

26. A device as in claim 24, wherein at least one of said radiation emitter and radiation receiver are provided at the tip of said hollow spiral.

27. A device an in claim 24, wherein one of said radiation emitter and radiation receiver is provided on the windings of said spiral needle and the other of said radiation emitter and radiation receiver is provided at the tip of said spiral needle.

28. A device as in claim 22, wherein said radiation emitter and radiation receiver are electro-optical converters.

29. A device as in claim 28, wherein said electro-optical converters are selected from the group consisting of incandescent lamps, light-emitting diodes and laser diodes.

30. A device as in claim 22, wherein the radiation emitter emits at least two different wavelengths which are received by the radiation receiver.

31. A method of in vivo measuring radiation transmitted through a portion of living tissue comprising the steps of:

providing a sensor device having at least two spaced sensor areas, at least one of said two sensor areas comprising at least one semiconductor, said semiconductor being housed within a sensor carrier formed as a hollow spiral and terminating with a point, at least one of the sensor areas constituting a radiation emitter and at least one of the other of the sensor areas constituting a radiation receiver;

screwing said hollow spiral type sensor carrier with said semiconductor into said tissue whereby the point and an end of said semiconductor enters said tissue to be transilluminated;

analyzing the radiation, in a spectral range between 0.1 $\mu$m and 20 $\mu$m, originating from the radiation emitter, transmitted through the tissue, to transilluminate said tissue between said two sensor areas; and sensing said transmitted radiation reaching the receiver.

32. A method for determining the concentration of a substance in pulsating blood, the method comprising the steps of:

provﬁﬁng at least two spaced sensor areas, at least one of which is a radiation emitter for emitting radiation, and at least one of which is a radiation sensor for receiving radiation;

invasively introducing at least one sensor area into living tissue carrying said pulsating blood such that a portion of said living tissue is between said spaced sensor areas; and emitting radiation from said radiation emitter and measuring the amount of radiation absorbed between said emitter and receiver;

wherein the radiation emitter and the radiation sensor are provided on separate carriers;

wherein the concentration of said substance influences the intensity of radiation received by the radiation sensor; and calculating the concentration of the substance in pulsating blood based on the measurement amount of radiation.

* * * * *